United States Patent [19]
Bollish et al.

[11] Patent Number: 5,957,885
[45] Date of Patent: *Sep. 28, 1999

[54] OXIMETRY MONITORED, PATIENT CONTROLLED ANALGESIA SYSTEM

[75] Inventors: Stephen J. Bollish, San Diego; Robert J. Duffy, Poway, both of Calif.

[73] Assignee: Alaris Medical Systems, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/744,486

[22] Filed: Nov. 6, 1996

[51] Int. Cl.⁶ .................................................. A61M 31/00
[52] U.S. Cl. ................................................................ 604/67
[58] Field of Search ................................ 604/30–31, 49, 604/50, 65–67, 118; 128/DIG. 12, DIG. 13

[56] References Cited

U.S. PATENT DOCUMENTS

| | | | |
|---|---|---|---|
| 4,697,593 | 10/1987 | Evans et al. | |
| 4,756,706 | 7/1988 | Kerns et al. | 604/66 |
| 4,898,578 | 2/1990 | Rubalcaba, Jr. | 604/66 |
| 5,069,668 | 12/1991 | Boydman | |
| 5,232,448 | 8/1993 | Zdeb | |
| 5,256,157 | 10/1993 | Samiotes et al. | 604/246 |
| 5,431,159 | 7/1995 | Baker et al. | |
| 5,431,627 | 7/1995 | Pastrone et al. | |
| 5,435,309 | 7/1995 | Thomas et al. | |
| 5,437,275 | 8/1995 | Amundsen et al. | |
| 5,451,408 | 9/1995 | Mezei et al. | |
| 5,713,856 | 2/1998 | Eggers et al. | 604/65 |

OTHER PUBLICATIONS

Ashburn et al., 1994, "Respiratory–Related Critical Events with Intravenous Patient–Controlled Analgesia," *Clinical Journal of Pain* 10:52–56.

Chauvin et al., 1993, "Equivalence of Postoperative Analgesia with Patient–Controlled Intravenous or Epidural Alfentanil," *Anesth. Analg.* 76:1251–8.

Doyle et al., 1993, "Comparison of Patient–Controlled Analgesia With and Without a Background Infusion After Lower Abdominal Surgery In Children," *British Journal of Anaesthesia* 71:670–673.

*Primary Examiner*—Michael Buiz
*Assistant Examiner*—Manuel Mendez
*Attorney, Agent, or Firm*—Pennie & Edmonds LLP

[57] ABSTRACT

A patient care system comprising an interface unit, a Patient Controlled Analgesia (PCA) unit, and a pulse oximetry unit is disclosed. The PCA unit provides PCA administration, including administration of a dose of analgesic upon request, and the pulse oximetry unit provides constant monitoring of the patient's blood oxygen saturation level and pulse rate. The interface unit provides for communication between and control of the PCA unit and the pulse oximetry unit, and further provides an interface between the user and the system. When the pulse oximetry unit indicates to the interface unit that the patient's blood oxygen saturation level and pulse rate has reached a user-specified minimum, the interface unit initiates visual and audio alarms and controls the PCA unit by shutting off the PCA unit. The interface unit also contains communication ports, which the interface unit can use to send signals to external devices, such as to alert alerts medical personnel.

21 Claims, 7 Drawing Sheets

102
| B | PULSE OX SETUP |

MIN SpO2 ____ %
MAX SpO2 ____ %
MIN PULSE ____ /min
MAX PULSE ____ /min
ANALGESIA MONITOR  ENABLED

>ENTER MINIMUM O₂ SATURATION OR RESTORE

RESTORE

FIG.5

102
| B | PULSE OX SETUP |

MIN SpO2  89%
MAX SpO2  99%
MIN PULSE  60/min
MAX PULSE  100/min
ANALGESIA MONITOR  ENABLED

>PRESS START TO BEGIN MONITORING

PCA AUTO SHUT-OFF        START

FIG.6

```
┌─────────────────────────┐
│ [A]  ANALGESIA          │
│ ┌──────┐        ┌─────┐ │
│ │DOSING│ ----   │ mcg │ │
│ │UNITS │        │ mg  │ │
│ ├──────┤ ----   │ mL  │ │
│ │CONCEN│        └─────┘ │
│ │TRATION│               │
│ └──────┘                │
│                         │
│   >SELECT DOSING UNITS  │
│       OR RESTORE        │
│                         │
│           [RESTORE]     │
└─────────────────────────┘
```

FIG.7

```
┌─────────────────────────┐
│ [A]  ANALGESIA          │
│ ┌──────┐                │
│ │DOSING│ mg             │
│ │UNITS │                │
│ ├──────┤                │
│ │CONCEN│ 10 mg/mL       │
│ │TRATION│               │
│ └──────┘                │
│                         │
│    >PRESS ENTER OR      │
│     NEXT TO CONTINUE    │
│                         │
│              [NEXT]     │
└─────────────────────────┘
```

FIG. 10

OXIMETRY MONITORED, PATIENT CONTROLLED ANALGESIA SYSTEM

FIELD OF THE INVENTION

The present invention relates to a programmable patient care system. Specifically, the present invention relates to a method and apparatus for centrally interfacing and controlling administration of analgesics in a patient controlled analgesia methodology while monitoring the patient to prevent central nervous system and respiratory depression associated with administration of analgesics.

BACKGROUND OF THE INVENTION

Patient Controlled Analgesia (PCA) is a method for delivering parenteral narcotics wherein a patient controls the administration of the narcotic analgesics, since the patient is usually in the best position to determine the need for additional pain control. PCA is commonly administered via a stand-alone type of infusion device dedicated solely for PCA use. Examples of PCA devices are disclosed in U.S. Pat. No. 5,069,668, to Boydman, and U.S. Pat. No. 5,232,448, to Zdeb.

The primary serious side effect of narcotic analgesics in the medical practice is central nervous system and respiratory depression which can result in serious brain damage or even death. However, PCA is a relatively safe means for administering narcotic analgesics, at least in theory, because if the patient self administers too much analgesic, the patient usually becomes drowsy and falls asleep. Thus, for the majority of the patients, PCA is a safe and effective means for pain control. Nonetheless, there have been cases of respiratory and central nervous system depression and even death associated with the administration of PCA. The causes include clinical errors in programming the PCA device, errors in mixing or labeling analgesics, device malfunction, and even overzealous relatives who administer extra doses of analgesics by pressing the dose request cord for the patient.

Despite the potential dangers of narcotic analgesic overdose, narcotic antagonists such as naloxone (Narcan) are widely available and commonly used in hospitals for reversal of respiratory and central nervous system depression. However, the effectiveness of such narcotic antagonists is highly dependent on prompt recognition and treatment of respiratory and central nervous system depression, as such depression can cause brain damage or even death due to lack of oxygen. Thus, respiratory and central nervous system depression must be recognized and treated promptly to assure a higher probability of successful recovery.

For detection of potential respiratory depression associated with the administration of narcotic analgesics, a system which indicates a patient's respiratory and cardiac status without the need to invasively measure or sample the patient's blood is particularly desirable and useful. Non-invasive pulse oximetry is one such method to monitor the oxygen saturation of a patient's blood and the patient's pulse rate. The combination of the blood oxygen saturation and pulse rate can be an important indicator of overall patient respiratory and cardiac status.

One common approach to non-invasive pulse oximetry uses a dual-wavelength sensor placed across a section of veinous tissue such as the patient's digit to measure the percentage of hemoglobin oxygenated in the arterial blood, and thereby measures the patient's oxygen saturation level. In addition, since the oxygenated hemoglobin at a specific tissue position is pulsatile in nature and synchronous with the overall circulatory system, the system indirectly measures the patient's pulse rate. Examples of similar pulse-oximetry sensors are disclosed in U.S. Pat. No. 5,437,275, to Amundsen et al., and U.S. Pat. No. 5,431,159, to Baker et al.

Patient care systems providing for central control of multiple pump units, potentially including PCA units, are known in the medical field. Examples of such systems are disclosed in U.S. Pat. No. 4,756,706 to Kerns et al., U.S. Pat. No. 4,898,578, to Rubalcabe, Jr., and U.S. Pat. No. 5,256,157, to Samiotes et al. Each of these prior art systems generally provides a controller which interfaces with a plurality of individual pumps to provide various control functions. An improved patient care system is disclosed in U.S. patent application Ser. No. 08/403,503 (U.S. Pat. No. 5,713,856) of Eggers et al. The central management unit of the Eggers et al. system can, for example, obtain infusion parameters for a particular infusion unit from the clinician and serve as an interface to establish the infusion rate and control infusion accordingly, individually control the internal setup and programming of each functional unit, and receive and display information from each functional unit. The Eggers et al. patient care system also provides for central control of various monitoring apparatus, such as pulse oximeters and heart monitors.

However, systems described above which are capable of controlling PCA and a pulse oximeter do not provide integrated control of the PCA device in conjunction with the pulse oximeter.

Such systems would require constant dedicated monitoring by medical personnel in order for prompt detection and treatment of potential respiratory depression side effect associated with the administration of narcotic analgesics. Thus, these systems are not cost-effective because of the added expense from constant monitoring by medical personnel.

Furthermore, the systems discussed above do not automatically shut-off of the PCA unit in the event of respiratory depression. Without automatic PCA shut-off, these systems actually allow further administration of the narcotic analgesics which can further aggravate the respiratory depression until appropriate medical personnel arrives to intervene. The time for medical personnel to arrive and intervene will delay administration of narcotic antagonists and thereby potentially compromise their effectiveness.

Because of disadvantages associated with existing PCA systems, certain patients who might otherwise benefit from the PCA method of therapy may not be PCA candidates because of concerns about respiratory depression. Even if a patient were eligible for PCA treatment with prior art systems, these systems do not allow the patient to receive a more aggressive treatment because of the risk of inadvertent respiratory depression and thus the patient would not be able to obtain quicker and more effective pain relief from a more aggressive treatment.

SUMMARY OF THE INVENTION

In view of the above problems and disadvantages of the prior art, it is an object of the present invention to provide a patient care system which reduces the risk and severity of respiratory depression and anoxic brain damage associated with PCA use.

It is also an object of the present invention to provide a patient care system which facilitates recognition and immediate notification of medical personnel of respiratory depression so as to increase system safety and cost effectiveness by reducing or eliminating the need for constant dedicated monitoring of a PCA patient for potential side effects by medical personnel.

It is a further object of the present invention to provide a patient care system which allows more patients to be candidates for PCA therapy who may otherwise not be considered for PCA therapy because of concerns about respiratory depression, and which allows eligible PCA patients to pursue a more aggressive PCA therapy so as to provide quicker and more effective pain relief while minimizing risks of inadvertent respiratory depression.

It is yet a further object of the present invention to provide a patient monitoring system capable of providing communication and interaction between a PCA unit and a pulse oximetry unit. The system would utilize signs of respiratory depression as recognized by the pulse oximeter unit and control the PCA unit accordingly. Thus, the risks of potentially severe respiratory depression resulting in anoxic brain damage associated with PCA use would be alleviated.

The patient care system of the present invention comprises a PCA unit, a pulse oximetry unit, and an interface between the two units. The interface may itself be a separate unit providing central management and communication and interaction between the PCA and pulse oximetry units. The system further comprises a PCA patient dose request cord which, when actuated, requests for administration of a bolus dose of narcotic analgesics to the PCA patient. In addition, a pulse oximetry sensor provides the signal to the pulse oximetry unit which uses the signal to determine a patient's percentage blood oxygen saturation and pulse rate.

In a preferred embodiment, both the PCA unit and the pulse oximetry unit are connected to and interfaced with the central unit to provide a safer system for delivering PCA while simultaneously monitoring for the potential side effects of respiratory depression associated with the administration of narcotic analgesics. The system of the present invention, upon detection and recognition of respiratory depression by the pulse oximetry unit, automatically and immediately shuts-off the PCA unit, sounds visual and audio alarms, as well as delivers appropriate feedback to appropriate medical personnel.

DETAILED DESCRIPTION OF THE INVENTION

The following preferred embodiments of the present invention are described generally in the context of the programmable modular patient care system disclosed in U.S. patent application Ser. No. 08/403,503, filed Mar. 13, 1995, and still pending, entitled Modular Patient Care System, filed by the assignee of the present application, and incorporated herein in its entirety by reference. However, a person skilled in the art will recognize that the disclosed methods and apparatus are readily adaptable for broader application, including but not limited to other patient care systems as described in the above referenced U.S. Patents to Kerns et al., to Rubalcabe, Jr., and to Samiotes et al. Moreover, as will also be appreciated by persons of ordinary skill in the art, an oximetry monitored, PCA system according to the invention can also be provided as a stand alone integral unit.

Figure 1:
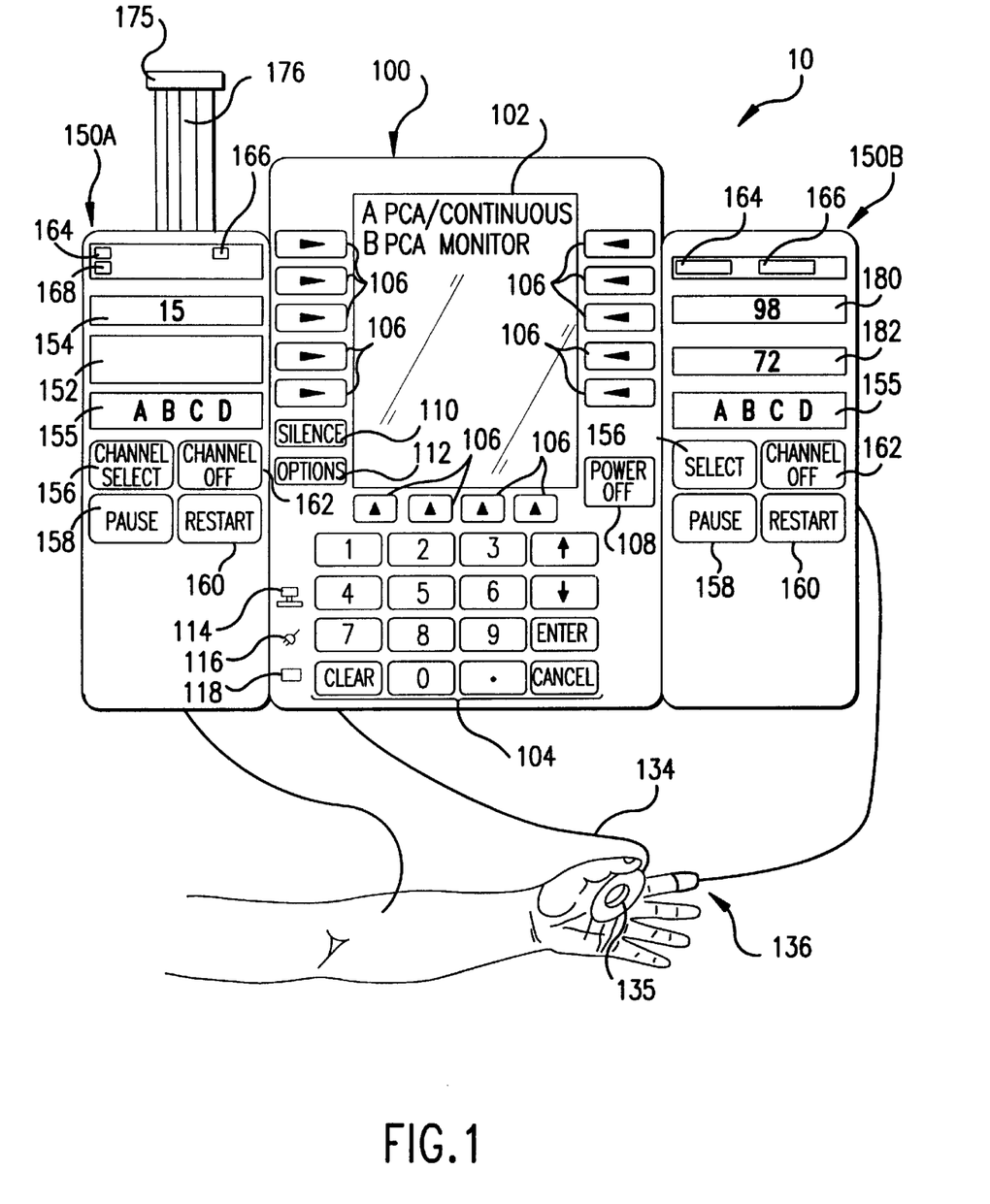
FIG. 1 is a front view of a system according to a preferred embodiment of the present invention.

FIG. 1 shows a front view of a modular, programmable patient care system 10 according to a preferred embodiment of the present invention. Patient care system 10 comprises central interface unit 100, PCA unit 150A, pulse oximetry unit 150B, PCA patient dose request cord 134, and pulse oximetry sensor 136. Although a preferred embodiment of the present invention has only two functional units, PCA unit 150A and pulse oximetry unit 150B, attached to central interface unit 100, system 10 may additionally comprise other functional units, depending on a patient's particular needs. Central interface unit 100 generally performs four functions in patient care system 10: (1) it provides a physical attachment of patient care system 10 to structures such as IV poles and bed rails, (2) it provides power supply to patient care system 10, (3) it provides an interface between system 10 and external devices, and (4) except for certain specific information, it provides a user interface of patient care system 10.

Central interface unit 100 contains information display 102, which may be used during setup and operating procedures to facilitate data entry and editing. Display 102 may also display various operating parameters during operation such as continuous dose, lockout interval and bolus dose for PCA unit 150A and for any other individual functional units which are pumps, minimum and maximum allowable percentage blood oxygen saturation and pulse rate for pulse oximetry unit 150B, as well as other prompts, advisories, and alarm conditions.

Central interface unit 100 also contains a plurality of hardkeys 104 for entering numerical data and, along with softkeys 106, for entering operational commands. In addition, central interface unit 100 further contains POWER ON hardkey 108 for turning on electrical power to central interface unit 100, SILENCE hardkey 110 for temporary disablement of the audio functionality of central interface unit 100, and OPTIONS hardkey 112 for allowing user access to available system or functional unit options. Central interface unit 100 may further contain external computer indicator 114 for indicating that system 10 is communicating with a compatible external computer system, external power indicator 116 to indicate that central interface unit 100 is connected to and operating with an external power source, and internal power indicator 118 to indicate that central interface unit 100 is operating with the use of an internal power source. Central interface unit 100 may also include a tamper-resistant control function (not shown) which can lock out a predetermined set of controls.

PCA unit 150A and pulse oximetry unit 150B each include channel position indicator 155 which identifies the channel position of the functional unit with respect to patient care system 10. For example, system 10 contains two channel positions A and B, with A to the immediate left of central interface unit 100 (such as PCA unit 150A of FIG. 1), and B to the immediate right of central interface unit 100 (such as pulse oximetry unit 150B of FIG. 1). Because both PCA unit 150A in channel A and pulse oximetry unit 150B in channel B are attached, as shown in FIG. 1, display 102 on interface unit 100 indicates A and B. When the desired functional unit is selected by depressing CHANNEL SELECT key 156 of a corresponding functional unit, display 102 is configured so as to act as the user interface for the selected functional unit. Specifically, display 102 is configured in accordance with a function specific domain to provide function specific displays and softkeys, as will become clear from the description of an example below.

Each functional unit has CHANNEL SELECT key 156 for selection of the functional unit, PAUSE key 158 (1) for pausing an infusion if the functional unit is a pump and if infusion is occurring or (2) for pausing a monitoring function if the functional unit is a monitoring unit, RESTART key 160 for resuming a previously paused infusion or monitoring function, and CHANNEL OFF key 162 for deselecting the channel, and, if the functional unit on the channel was the only functional unit operating, for powering off system 10. In addition, PCA unit 150A and pulse oximetry unit 150B each contain ALARM indicator 164 to indicate alarm condition and STANDBY indicator 166 to indicate standby condition. PCA unit 150A additionally contains INFUSING indicator 168 to indicate infusing condition. Each indicator illustratively illuminates when the respective functional unit is in the respective condition.

PCA unit 150A contains channel message display 152, which may be used to display informational, advisory, alarm, or malfunction messages, and rate display 154 which may be used to display, for example, the infusion rate at which the PCA unit is operating or the lockout interval. PCA unit 150A may also include a door lock (not shown) for providing security for enclosed narcotics or other medication to be infused. For electromechanical fluid infusion, PCA unit 150A also contains syringe pusher 175 and syringe 176. PCA unit 150A further includes an infusion pumping device within its housing which infuses bolus doses of narcotic analgesics in response to commands from central interface unit 100. As known in the prior art, PCA unit 150A can be either a syringe based pumping system, a large volume parenteral type of pumping system, or other appropriate configurations as can be readily determined by one skilled in the art. PCA unit 150A includes standard pumping and safety mechanisms to control various functions performed by the pumping device such as control of fluid delivery to the patient and monitoring of fluid path for occlusion or air-in-line.

Connected to pulse oximetry unit 150B is pulse oximetry sensor 136 which is also attached to a section of a patient's veinous tissue, such as the digit, where sensor 136 can send and receive various signals. Sensor 136 sends these signals to pulse oximetry unit 150B which interprets the signals in accordance with the standard operation of a pulse oximeter as will be understood by persons of ordinary skill in the art. From these signals, pulse oximetry unit 150B can determine the patient's percentage blood oxygen saturation and pulse rate. Pulse oximetry unit 150B contains SpO2% display 180 to display the patient's percentage oxygen saturation and Pulse display 182 to display the patient's pulse rate.

Figure 2:
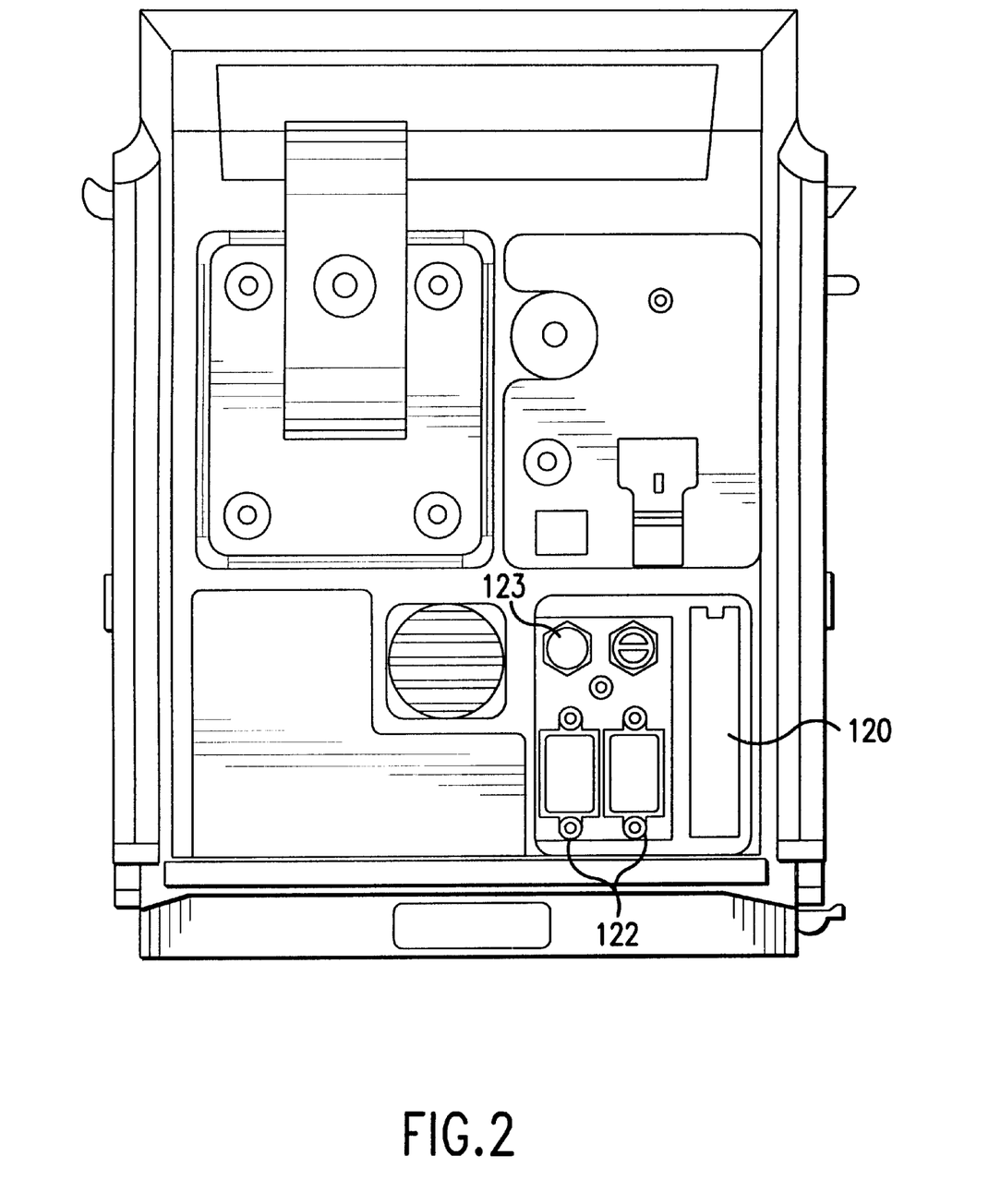
FIG. 2 is a back view of a central interface unit of the patient care system of FIG. 1.

Referring now to FIG. 2, at the back of central interface unit 100 is at least one external communication interface 120, at least one interface port 122, and at least one PCA port 123. External communication interface 120 and interface port 122 may be used to download and upload information and data and may also act as an interface to patient monitoring networks and nurse call systems, or as an interface to external equipment such as barcode readers to provide a means of inputting drug and/or patient information from medication or patient records. Performing these functions with external communication interface 120 and interface ports 122 provide greater functionality and adaptability, cost savings, and reduction in input error. In particular, clinical error associated with programming of PCA unit 150A would be reduced, thereby reducing the risks of respiratory depression associated with the administration of narcotic analgesics from use of PCA unit 150A.

PCA port 123 provides a connection between central interface unit 100 and one end of PCA patient dose request cord 134. At an opposite end of PCA patient dose request cord 134 is hand-held dose request PCA button or other PCA actuation device 135, which can be actuated to request a dose of analgesic for the PCA patient. It is to be understood that although central interface unit 100 contains PCA port 123 in the preferred embodiment, PCA unit 150A may also contain PCA port 123 (not shown) which would provide a similar connection from PCA unit 150A, through PCA patient dose request cord 134, to dose request actuation device 135.

Figure 3:
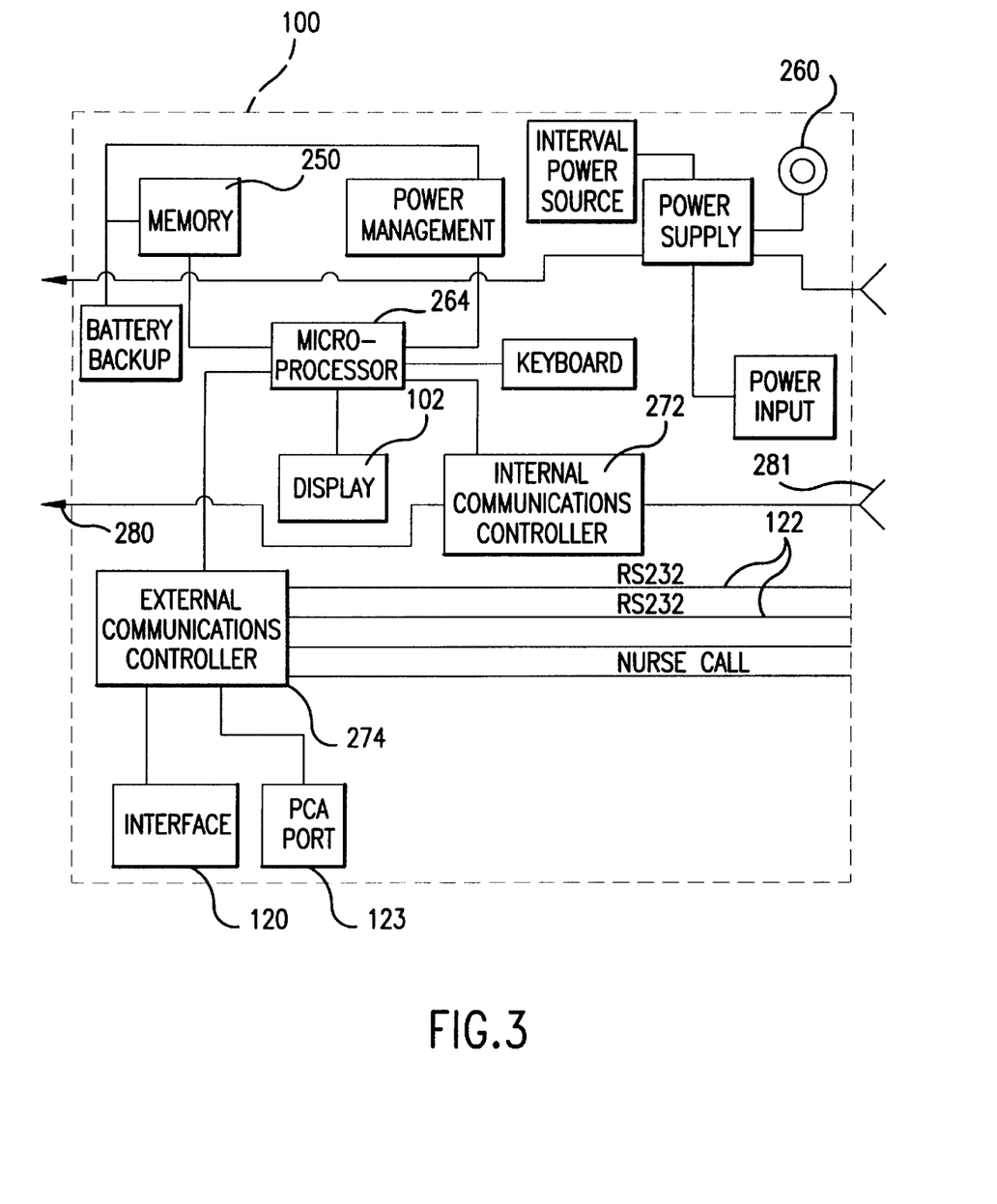
FIG. 3 is a block diagram of a central interface unit of the present invention.

Referring now to FIG. 3, depicting a block diagram of central interface unit 100 of the present invention, microprocessor 264 receives and processes data and commands from the user and communicates with functional units and other external devices. Microprocessor 264 directly controls External Communication Controller 274 which controls PCA port 123 and data flow through interface ports 122 and/or external communication interface 120. Microprocessor 264 also controls internal communications controller 272 which controls internal communication ports 280 and 281. Internal communication ports 280 and 281 are included in each functional unit as well as central interface unit 100 and provide data and command interfaces between central interface unit 100 and attached functional units.

During operation of system 10, when dose request PCA actuation device 135 is actuated, microprocessor 264 receives the dose request signal via patient dose request cord 134 and PCA port 123. If microprocessor 264 determines that there are no limitations in administering a bolus dose of narcotic analgesics, microprocessor 264 would then send a signal to PCA unit 150A, via internal communications controller 272 and internal communication port 280 and/or port 281, instructing PCA unit 150A to administer the bolus dose.

Microprocessor 264 also provides for the coordination of activities between PCA unit 150A and pulse oximetry unit 150B. For example, a clinician may set up system 10 with PCA unit 150A to provide PCA administration and pulse oximetry unit 150B to monitor oxygen saturation and pulse rate of a PCA patient. The clinician may specify a minimum or maximum percentage blood oxygen saturation and a minimum or maximum pulse rate. If the PCA patient's blood oxygen saturation or pulse rate becomes less than the minimum or greater than the maximum levels set by the clinician, pulse oximetry unit 150B would send a signal to microprocessor 264 via internal communications controller 272 and internal communication port 280 and/or port 281. In response, microprocessor 264 may activate audio alarm 260, send a visual alarm to display 102, and/or shut off PCA unit 150A to cease all further administration of analgesics until after the exceedingly low or high blood oxygen saturation and/or pulse rate situation is reconciled, such as by clinician intervention. Alternatively, microprocessor 264 may simply lock-out use of PCA actuation device 135 so that the patient cannot provide further self-administrations. Thus, after appropriate values have been set up, central interface unit 100 provides communication and coordination between PCA unit 150A and pulse oximetry unit 150B to ensure greater safety and decreased risk of injuries from respiratory depression.

The interactions and functions of central interface unit 100, PCA unit 150A, and pulse oximetry unit 150B will now be described in conjunction with FIGS. 4–10 which show some of the step-by-step states of information display 102 during setup and operation of system 10.

Figure 4:
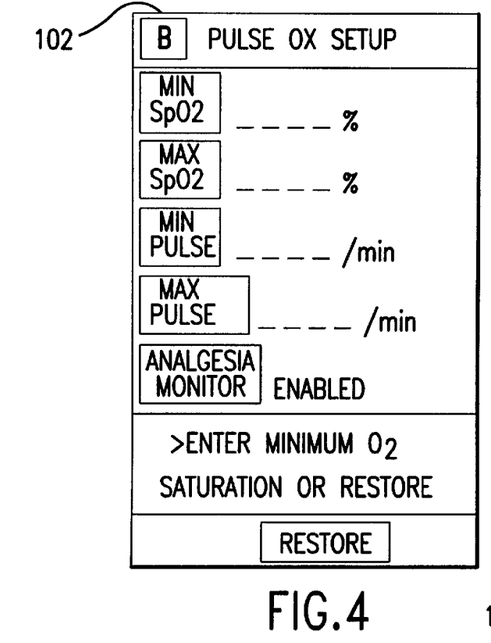
FIG. 4 depicts an information display of central interface unit during setup of pulse oximetry unit.

To set up the preferred embodiment of system 10, the clinician first attaches an appropriate end of pulse oximetry sensor 136 to pulse oximetry unit 150B and an opposite end to an external patient site containing veinous tissue, such as the patient's digit, as shown in FIG. 1. The clinician then selects pulse oximetry unit 150B and its corresponding channel by pressing SELECT key 156 on pulse oximetry unit 150B. By selecting pulse oximetry unit 150B, information display 102 is configured so as to act as the user interface and thus provides pulse oximetry function specific displays and softkeys, as shown in FIG. 4. The clinician can either input the minimum and maximum values or restore the previous values for percentage blood oxygen saturation and pulse rate levels.

Figure 5:
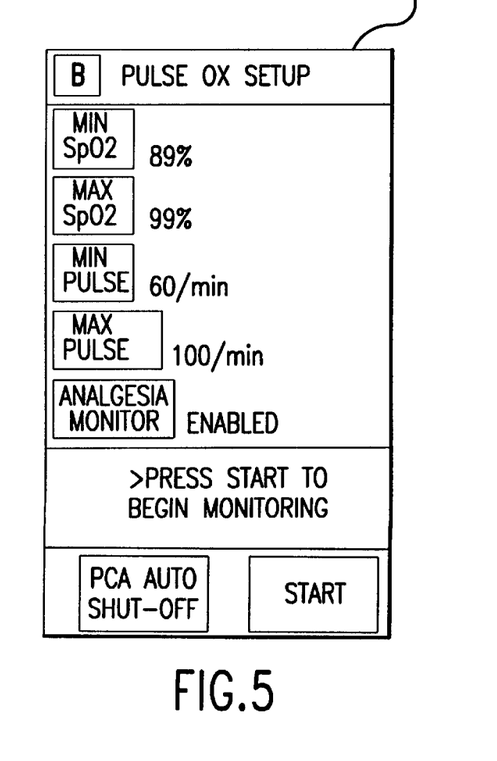
FIG. 5 depicts another information display of central interface unit during setup of pulse oximetry unit.

FIG. 5 shows information display 102 after the clinician has entered or recalled previous values. Prior to starting pulse oximetry monitoring, the clinician may select the auto shut-off option for one or more other functional units, such as PCA unit 150A, so that central interface unit 100 shuts-off the selected functional unit(s) if the patient's blood oxygen saturation level or pulse rate falls outside of the specified maximum and minimum levels. Once pulse oximetry monitoring starts, the patient's percent blood oxygen saturation and pulse rate are displayed in SpO2% display 180 and Pulse display 182, respectively, as previously described and shown in FIG. 1. Although the preferred embodiment patient care system 10 automatically initiates both audio and visual alarms as well as notifies medical personnel, such as triggering a nurse call, if the patient's percent blood oxygen saturation or pulse rate falls above or below specified maximum or minimum levels, system 10 can be configured such that the clinician can also select specific alarms and notification to medical personnel in such an event.

Figure 6:
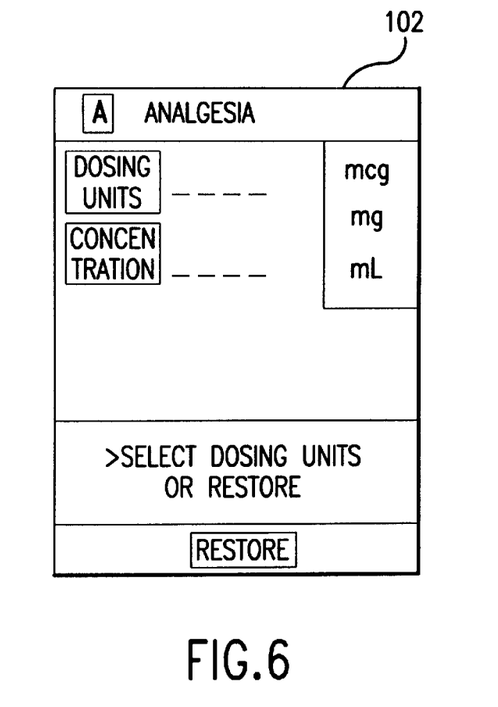
FIG. 6 depicts another information display of central interface unit during setup of PCA unit.
Figure 7:
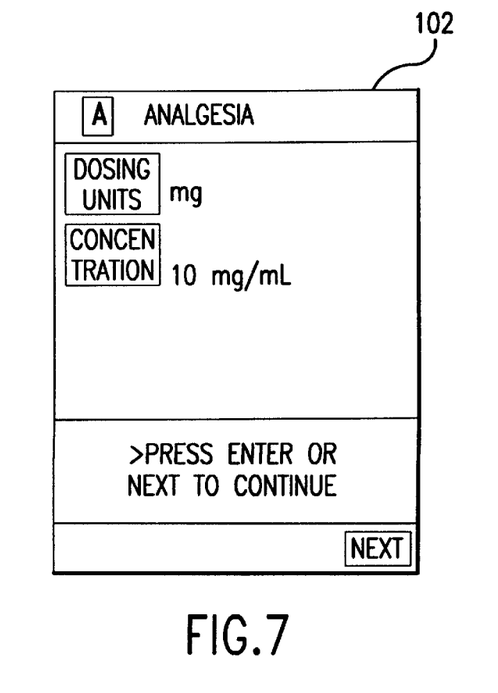
FIG. 7 depicts another information display of central interface unit during setup of PCA unit.
Figure 8:
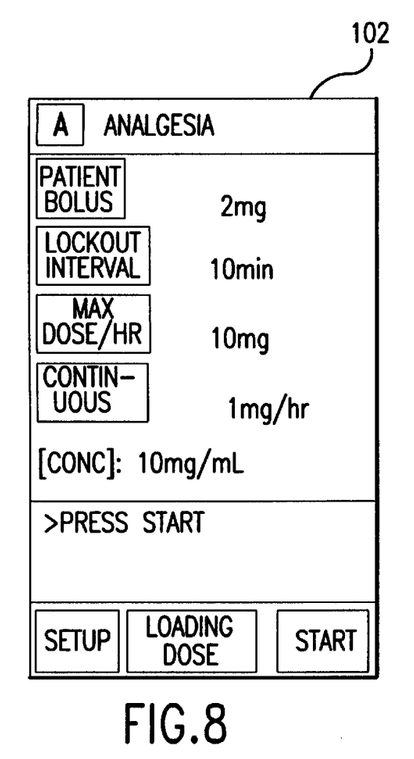
FIG. 8 depicts an information display of central interface unit after completion of setup and during operation.

The clinician then selects PCA unit 150A and its corresponding channel by depressing SELECT key 156 on PCA unit 150A. By selecting PCA unit 150A, information display 102 is configured so as to act as the user interface and thus provides PCA function specific displays and softkeys, as shown in FIGS. 6–8. The clinician may first restore previous dosing units and analgesics concentration or select the dosing units from, for example, mcg, mg, or mL, and input the analgesics concentration, as shown in FIG. 6 and 7. Next, as shown in FIG. 8, the clinician may input or restore previous parameters for patient bolus dosage. For additional precaution to further prevent respiratory and central nervous system depression and as an alternative embodiment of the present invention, system 10 or PCA unit 150A may require the clinician to enter patient request dosing limits, such as maximum dose per hour or per 24-hour period.

After entering the patient bolus dosage parameters, the clinician may choose to administer a background continuous infusion of narcotic analgesics by pressing softkey 106 adjacent to CONTINUOUS. Use of a background infusion in combination with patient requested doses provides a level of narcotic analgesia sufficient for periods of low activity such as when the patient is sleeping. Thus, when the patient wakes up and requires additional analgesia because of increased activity levels, the patient can self-administer additional narcotic analgesics to meet those needs. If a background continuous infusion is selected by pressing softkey 106 adjacent to CONTINUOUS, display 102 allows the clinician to input desired continuous infusion dose. FIG. 8 shows information display 102 after the clinician has entered values for both patient bolus dose and continuous dose.

Once the above steps have been completed, the clinician attaches PCA administration set to the patient's indwelling vascular access device (not shown) and presses softkey 106 adjacent to START on central interface unit 100. PCA unit 150A is now operating with continuous monitoring by pulse oximetry unit 150B of the patient's percentage blood oxygen saturation and pulse rate. PCA unit 150A begins background continuous infusion, if one has been selected. In addition, the patient may now request a dose of narcotic analgesics at any time by means of patient dose request actuation device 135. Of course, whether the patient actually receives a requested dose depends upon the patient request dosing limits, if any, as well as the patient's current percent blood oxygen saturation and pulse rate relative to the minimum levels set by the clinician.

Figure 9:
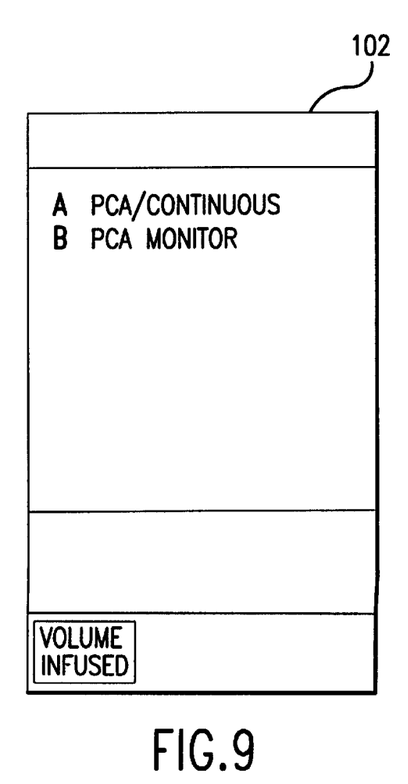
FIG. 9 depicts an information display of central interface unit with patient care system in alarm mode.

Referring now to FIG. 9, positions A and B in information display 102 advises the clinician that the two functional units located at channel positions A and B are communicating with central interface unit 100. Information display 102 may further be used to indicate the status of each functional unit occupying each respective channel in system 10. For example, display 102 at channel A, corresponding to PCA unit 150A occupying channel A, can be configured to indicate the patient bolus dosage and background continuous infusion dosage. In addition, display 102 at channel B, corresponding to pulse oximetry unit 150B occupying channel B, can be configured to indicate minimum and maximum percentage oxygen saturation and pulse rate levels. System 10 may also be configured such that display 102 at channel B displays the patient's current percent blood oxygen saturation and pulse rate.

Figure 10:
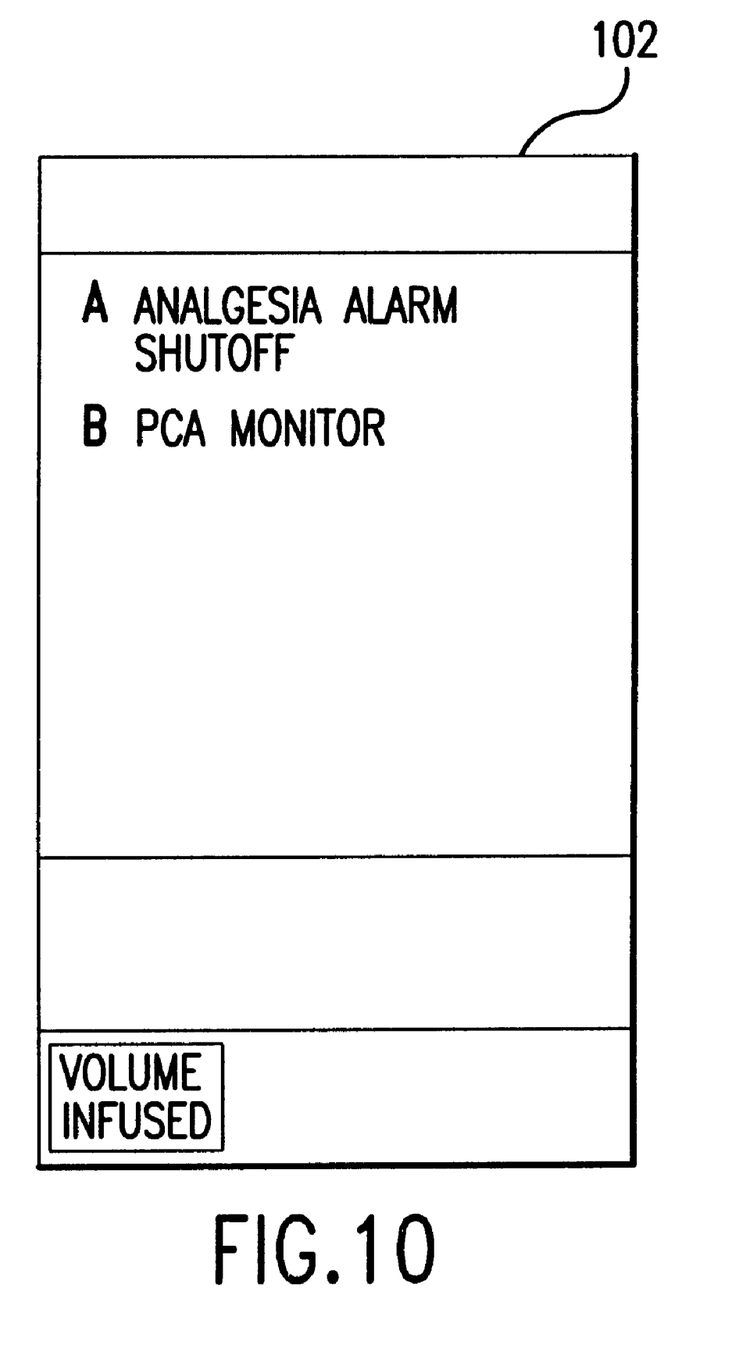
FIG. 10 depicts an information display of central interface unit illustrating alarm shutoff status.

In the event that the patient's percent blood oxygen saturation and pulse rate is outside of the maximum and minimum levels set by the clinician, central interface unit 100 immediately shuts-off PCA unit 150A, and thereby stops further administration of any background infusion and bolus doses. As illustrated in FIG. 10, position A of display 102 indicates ANALGESIA ALARM SHUTOFF status for PCA unit 150A. In addition, central interface unit 100 activates audio alarm 260, displays visual alarm on information display 102, flashes ALARM indicator 164 on PCA unit 150A and/or pulse oximetry unit 150B, and sends an emergency signal via interface ports 122 and external communications controller 274 in order to alert appropriate medical personnel. Thus, faster response and intervention by medical personnel of the patient's respiratory depression from the administration of narcotic analgesics is allowed.

Although various embodiments of the invention have been described, the descriptions are intended to be merely illustrative. Thus, it will be apparent to those skilled in the art that modifications may be made to the embodiments as described without departing from the scope of the claims set forth below.

We claim:

1. A patient care system, comprising:
a pump capable of intravenous delivery of analgesia to a patient;

patient control means for permitting the patient to self-administer analgesia using said pump; and a monitor to monitor the patient's blood oxygen saturation, said monitor cooperating with said delivery of analgesia to automatically prevent administration of analgesia using the patient control means in response to the patient's blood oxygen saturation falling outside predetermined levels as measured by said monitor, said monitor comprising a pulse oximiter.

2. The system according to claim 1, wherein said monitor further monitors patient pulse rate; and said monitor cooperates with the pump to automatically prevent administration of analgesia using the patient control means when the pulse rate falls outside predetermined levels.

3. The system according to claim 1, further comprising interface means between said pump and said monitor, said interface means including a processor means providing communication between the pump and monitor and providing said cooperation between said delivery of analgesia and said monitor.

4. A patient care system, comprising:

an interface unit;

a first functional unit capable of delivering patient therapies to a patient in accordance with first functional unit specific information, said first functional unit removably connected to the interface unit and communicating therewith; and a patient therapy request actuator connected to the system and cooperating with the first functional unit, wherein actuation of said patient therapy request actuator normally results in delivery of a predetermined patient therapy by the first functional unit;

a second functional unit capable of monitoring conditions of the patient in accordance with second functional unit specific information, wherein a user specifies limits for the patient conditions, said second functional unit removably connected to the interface unit and communicating therewith;

wherein the interface unit determines if the patient conditions received from the second functional unit are within said user specified limits, and wherein the interface unit executes a termination command to terminate patient therapy delivery by the first functional unit in response to patient conditions outside said user specified limits.

5. The patient care system of claim 4, wherein said termination command locks out operation of the patient therapy request actuator.

6. The patient care system of claim 4, wherein the second functional unit monitors patient blood oxygen saturation level and pulse rate.

7. The patient care system of claim 4, further comprising an audio alarm, wherein when the interface unit determines that the patient conditions are not within said user specified limits, the interface executes an alarm command to activate said audio alarm.

8. The patient care system of claim 4 further comprising at least one visual alarm, and wherein when the interface unit determines that the patient conditions are not within said user specified limits, the interface executes an alarm command to activate said at least one visual alarm.

9. The patient care system of claim 4, wherein said interface unit comprises:

a user interface adapted to provide an interface between the system and the user of the system;

an interface display; and an interface keyboard, including a plurality of softkeys interacting with the interface display such that the user interface is configured in accordance with the functional unit specific information to provide predetermined command options to the user corresponding to said functional unit;

wherein the interface unit permits the user to input the user specified limits for the patient conditions into the system.

10. A patient care system, comprising:

an interface including a microprocessor and a user interface adapted to provide an interface between the system and a user of the system, said interface including means for receiving patient condition limits and dosage parameters;

a dosage request actuator;

a pump unit communicating with said interface for delivering intravascular analgesics to a patient in response to actuation of said dosage request actuator, said delivery being in accordance with dosage parameters received from said interface;

a patient monitoring unit communicating with said interface, said monitoring unit including a sensor contactable with the patient for monitoring conditions of the patient including blood oxygen saturation level and pulse rate, said monitoring unit providing at least one signal to the interface indicative of said patient conditions;

wherein the interface microprocessor compares said patient condition signal to patient condition limits input by a user and terminates analgesic delivery by the pump unit in response to patient conditions outside said patient condition limits.

11. The patient care system of claim 10, further comprising at least one alarm wherein when the interface microprocessor determines that the patient conditions are outside specified limits, the interface microprocessor executes an alarm command to activate said alarm.

12. The patient care system of claim 10, wherein said dosage parameters comprise bolus dose delivery parameters including bolus dose, duration, and rate.

13. The patient care system of claim 12, wherein the dosage parameters further comprise one or more patient request dosage limits, selected from the group comprising minimum interval of time between doses, maximum total number of doses, maximum number of bolus doses over a predetermined period of time, and maximum total volume of patient therapy to be infused.

14. The patient care system of claim 12, wherein the pump unit additionally delivers a continuous infusion to the patient and wherein the dosage parameters further comprise continuous infusion rate and volume to be infused.

15. A method for controlling patient self-administration of fluid infusions comprising, monitoring patient conditions by connecting a patient monitoring unit to the patient, wherein the patient monitoring unit is capable of monitoring conditions of the patient;

connecting the monitoring unit to an interface unit including a microprocessor and a user interface adapted to provide an interface with a user;

inputting patient condition limits into the interface unit;

comparing monitored patient conditions to patient condition limits in said interface and generating a signal indicative of said comparison;

connecting the patient to an infusion unit, wherein the infusion unit communicates with the interface unit, said infusion unit is capable of performing fluid infusion to the patient in accordance with infusion unit specific information;

requesting fluid infusions from the infusion unit by patient activation of the infusion unit;

performing fluid infusion with the infusion unit in accordance with a predetermined infusion protocol in response to said patient activation and in response to a signal from the interface unit representative of the monitored patient conditions being within said patient condition limits; and disabling the infusion unit and terminating the fluid infusion in response to a signal from the interface unit representative of the monitored patient conditions being outside the patient condition limits.

16. The method of claim 15, wherein the monitoring step comprises monitoring the patient's blood oxygen saturation level and pulse rate; and wherein the patient condition limits are minimum blood oxygen saturation level and minimum pulse rate.

17. The method of claim 15, wherein the monitoring step comprises monitoring the patient's blood oxygen saturation level and pulse rate; and wherein the patient condition limits are maximum blood oxygen saturation level and maximum pulse rate.

18. The method of claim 15, wherein the predetermined infusion protocol for the infusion unit comprises bolus dose delivery parameters including bolus dose, duration of bolus dose infusion, and rate of bolus dose infusion.

19. The method of claim 15, wherein the predetermined infusion protocol for the infusion unit further comprises one or more patient request dosage limits, selected from the group comprising minimum interval of time between doses, maximum total number of doses, maximum number of bolus doses over a predetermined period of time, and maximum total volume of patient therapy to be infused.

20. The method of claim 15 further comprising the step of providing a continuous infusion by the infusion unit.

21. A method for controlling patient use of analgesia in systems where the patient self-administers analgesia utilizing a patient dose request actuator to actuate a patient actuatable pump, comprising:

continuously monitoring patient conditions including pulse rate and blood oxygen saturation level;

identifying at least one of said patient conditions as being outside predetermined acceptable levels; and automatically disabling, without clinical intervention, at least one of the patient dose request actuator and pump in response to said identification, to prevent patient actuation of the patient actuatable pump.

* * * * *